US010052424B2

(12) United States Patent
Rohde et al.

(10) Patent No.: US 10,052,424 B2
(45) Date of Patent: Aug. 21, 2018

(54) EXTRACORPOREAL BLOOD TREATMENT SYSTEM WITH HEAT RECOVERY

(71) Applicant: B. BRAUN AVITUM AG, Melsungen (DE)

(72) Inventors: Alexander Rohde, Melsungen (DE); Siegmar Rott, Kassel (DE); Bjoern Broeker, Staufenberg (DE)

(73) Assignee: B. BRAUN AVITUM AG, Melsungen (DE)

( * ) Notice: Subject to any disclaimer, the term of this patent is extended or adjusted under 35 U.S.C. 154(b) by 616 days.

(21) Appl. No.: 14/332,012

(22) Filed: Jul. 15, 2014

(65) Prior Publication Data
US 2015/0021245 A1    Jan. 22, 2015

(30) Foreign Application Priority Data
Jul. 18, 2013  (DE) .......................... 10 2013 107 672

(51) Int. Cl.
*B01D 35/00*    (2006.01)
*A61M 1/16*    (2006.01)

(52) U.S. Cl.
CPC ........ *A61M 1/1629* (2014.02); *A61M 1/1662* (2014.02); *A61M 1/1664* (2014.02); *A61M 1/1672* (2014.02); *A61M 1/1686* (2013.01); *A61M 2202/0413* (2013.01); *A61M 2205/15* (2013.01); *A61M 2205/3334* (2013.01); *A61M 2205/3368* (2013.01); *A61M 2205/366* (2013.01)

(58) Field of Classification Search
None
See application file for complete search history.

(56) References Cited

U.S. PATENT DOCUMENTS

| 4,351,731 | A | 9/1982 | Perrot |
| 4,715,959 | A | 12/1987 | Allan et al. |
| 4,804,474 | A | 2/1989 | Blum |

(Continued)

FOREIGN PATENT DOCUMENTS

| CN | 204016958 U | 12/2014 |
| EP | 1 440 041 | 10/2009 |

(Continued)

OTHER PUBLICATIONS

European Search Report for EP 14 17 7206 dated Mar. 31, 2015.
(Continued)

*Primary Examiner* — Richard C Gurtowski
(74) *Attorney, Agent, or Firm* — RatnerPrestia

(57) ABSTRACT

Blood treatment/dialysis systems are disclosed. The systems include a water treatment unit, preferably of the reverse osmosis type, whose outlet has connected thereto a water supply line provided with a number of branch connections having fluidly coupled thereto blood treatment/dialysis machines in a selective manner, and a drain line through which exhausted blood treatment fluid can be discharged from fluidly coupled blood treatment/dialysis machines. Also disclosed is a machine-external heat exchanger, which is connected to the water supply line upstream of the branch connections on one side and to the drain line on the other side.

17 Claims, 1 Drawing Sheet

(56) References Cited

U.S. PATENT DOCUMENTS

| | | | |
|---|---|---|---|
| 6,818,179 B1* | 11/2004 | Edgson | A61L 2/04 210/143 |
| 2011/0192796 A1 | 8/2011 | Smejtek et al. | |
| 2013/0056419 A1 | 3/2013 | Curtis | |
| 2013/0126430 A1 | 5/2013 | Kenley et al. | |
| 2014/0014580 A1 | 1/2014 | Ritter | |
| 2015/0021245 A1 | 1/2015 | Rohde et al. | |

FOREIGN PATENT DOCUMENTS

| | | |
|---|---|---|
| WO | WO 00/74833 | 12/2000 |
| WO | WO 2012/119799 | 9/2012 |
| WO | WO 2012/175210 | 12/2012 |

OTHER PUBLICATIONS

German Search Report for DE 10 2013 107 672.6 dated Mar. 25, 2014.

Chinese Office Action for Chinese Application No. 201410344892.7, dated Jun. 23, 2017, including English translation, 14 pages.

* cited by examiner

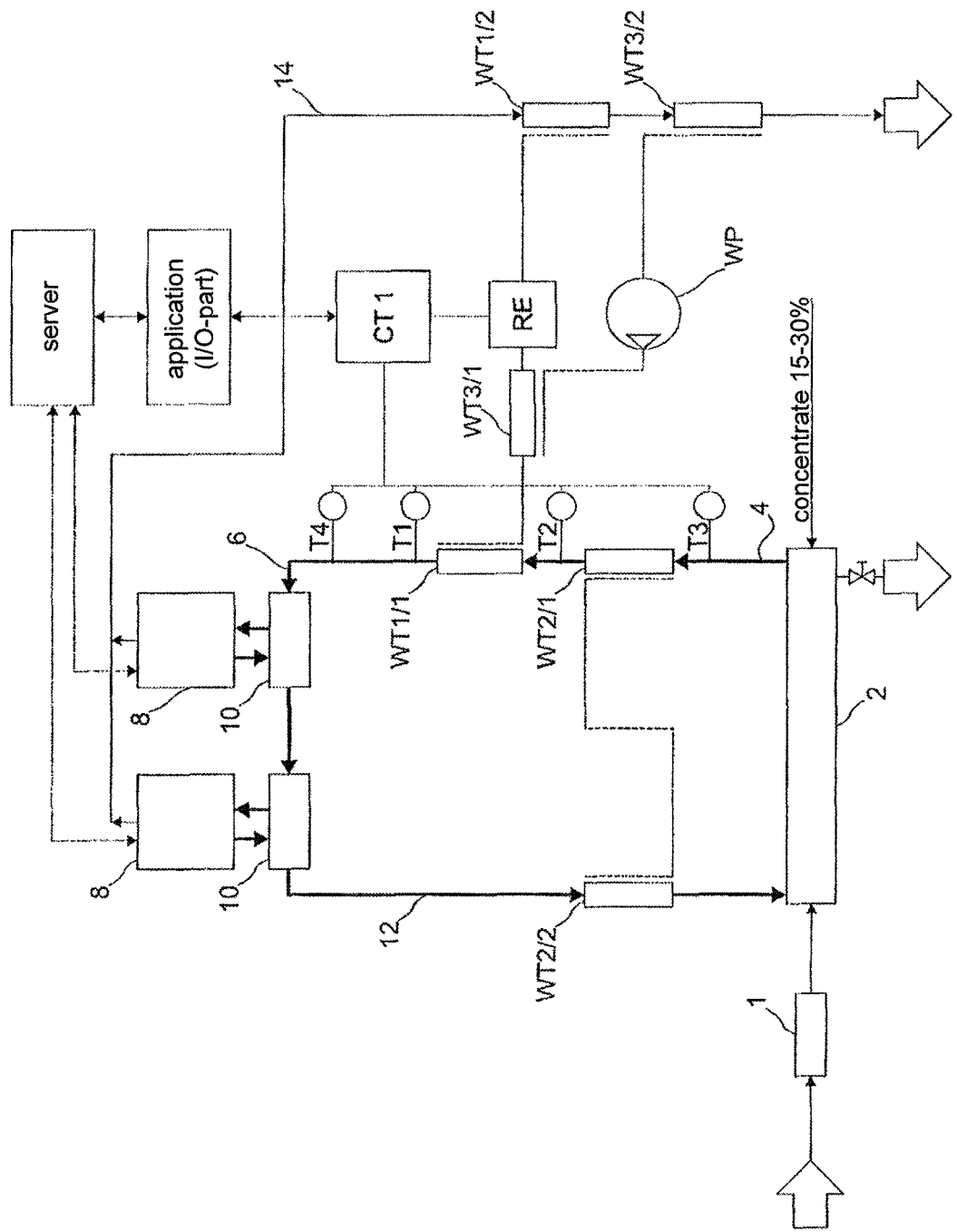

EXTRACORPOREAL BLOOD TREATMENT SYSTEM WITH HEAT RECOVERY

CROSS REFERENCE TO RELATED APPLICATIONS

This application claims priority to German application DE 10 2013 107 672.6 filed Jul. 18, 2013, the contents of such application being incorporated by reference herein.

FIELD OF THE INVENTION

The present invention relates to an extracorporeal blood treatment system, in particular a dialysis system, with heat recovery and central power management, and in addition to an extracorporeal blood treatment system, in particular a dialysis system, comprising a stationary water/fluid supply and blood treatment machines (dialysis machines), preferably of mobile construction, which can selectively be connected thereto.

BACKGROUND

Extracorporeal blood treatment systems, preferably dialysis systems of the type in question, generally consist of a stationary water supply with a number of water connection facilities (tap connections), which are adapted to have selectively connected thereto preferably mobile blood treatment/dialysis machines (machines for acute dialysis, machines for apheresis, etc.) for fluid communication therewith. Such blood treatment/dialysis machines are provided with internal heating systems, among other components, so as to heat the water tapped from the stationary water supply to body temperature in the blood treatment/dialysis phase and to a temperature slightly below boiling temperature (e.g. approx. 70° C.-90° C.) in the disinfection phase. The amount of primary energy required for this purpose is made available to the blood treatment/dialysis machines in the form of electric current. In addition, the blood treatment/dialysis machines may each be provided with integrated heat exchangers so as to supply thermal energy that is present in the exhausted cleaning/dialysis fluid to the water tapped from the stationary water supply or to the fresh cleaning/dialysis fluid prepared therefrom, thus reducing the amount of primary energy consumed by the individual blood treatment/dialysis machines.

Therefore, these known concepts are substantially based on the so-called isolated solution principle in the form of blood treatment/dialysis machines which work in a fully independent manner and provide, each individually (separately), the necessary operating materials, such as disinfectants or the cleaning/dialysis fluid, etc., in the respective suitable state (temperature, concentration) as well as at respective suitable moments in time.

DESCRIPTION OF THE RELATED ART

As has already been outlined hereinbefore, the cleaning fluid flowing through the cleaning filter in extracorporeal blood treatment processes must be heated to a preset target temperature—normally to a temperature of approx. 37° C. In a dialysis machine this is done in that the incoming dialysis fluid/water is first preheated by the above mentioned internal heat exchanger and then heated, preferably electrically, by a heater until the target value is reached. Equipping each blood treatment/dialysis machine with a heat exchanger is, however, complicated and also expensive. Depending on the number of blood treatment/dialysis machines connected, the whole blood treatment system is therefore rendered increasingly cost-intensive. If, however, the use of an internal heat exchanger were dispensed with, this would lead to an unacceptable increase in the operating costs due to an increasing consumption of primary energy.

WO 2012/175210 A2 suggested an energy supply concept that intends, in principle, to provide primary energy generated at a reasonable price and consumed e.g. in a dialysis center equipped with a dialysis system whose structural design corresponds to the above mentioned one. Accordingly, e.g. a photovoltaic system for generating electric current is combined with a heat pump, in particular for heating treatment rooms. To this end, said heat pump takes up thermal energy from a discharge line used for exhausted dialysis fluid and transfers useful energy to the treatment rooms. The energy contained in the exhausted dialysis fluid can thus be recycled with the heat pump. The isolated solution principle described at the beginning and concerning the individual dialysis machines remains, however, unchanged.

SUMMARY OF THE INVENTION

Taking into account this prior art, it is an object of the present invention to provide an energy supply concept for an extracorporeal blood treatment center (such as a dialysis center), with which the total running operating costs of the extracorporeal blood treatment center can be reduced.

This object is achieved by a blood treatment system (such as a dialysis system) having features set forth herein.

Aspects of the present invention are based on the following energetic considerations:

The improvement of the operational efficiency of a blood treatment center (dialysis center) is not limited to the provision of primary energy generated at a reasonable price and the recycling of energy that has already been deployed with known energy conversion systems, but it also concerns the advantageous use of such energy. To this end, it is necessary to analyze the monetary expenses in a blood treatment center (dialysis center) for provision, maintenance and day-to-day operation and to optimize them by adequately centralizing the energy deployed.

For example, especially in the case of blood treatment/dialysis machines, the provision of each individual of these machines with a heat exchanger may lead to an increase in costs, in particular with respect to provision and maintenance (including disinfection of the heat exchanger). Although it is known that operating costs accruing parallel thereto, e.g. for heating the dialysis center, can be reduced e.g. by alternative energy conversion systems according to the prior art, the question arising here in connection with the present invention is whether the resultant saving of costs is higher or lower than the above mentioned increase in costs. Especially on the basis of individual economic analyses it may therefore be of advantage to use the recyclable/recycled thermal energy for other purposes, such that machine-internal heat exchangers can perhaps be dispensed with or that their dimensions can at least be reduced in size.

According to the latest findings, the individual operation of the blood treatment/dialysis machines may lead to a situation in which blood treatment/dialysis machines are accidentally operated in identical operating phases, e.g. in a disinfection phase with high power consumption. This leads to temporary power consumption peaks, which, for reasons of power tariff, may result in excessive power rates. The use of the possibly recycled primary energy should therefore be configured and, e.g. with a special data management system, be controlled such that the operation of the blood treatment/dialysis machines, which have hitherto only been operated individually, can be coordinated so as to avoid, or at least reduce such consumption peaks.

According to a first aspect of the present invention, which may optionally be claimed as an independent aspect, the blood treatment/dialysis system is, in its stationary section, provided with a (central) water treatment unit, preferably of the reverse osmosis type, which has supplied thereto fresh (tap) water, i.e. feed water, and the outlet of which has connected thereto at least one water supply line or fluid supply line for (non-stationary) blood treatment/dialysis machines, said supply line including a section having a number of branch connections. These branch connections have or are adapted to have fluidly coupled thereto in a selective manner blood treatment/dialysis machines (also machines for acute dialysis, machines for apheresis, etc.), said machines being preferably of mobile construction. As regards their structural design, these machines essentially correspond to machines that are known from the prior art, but, according to the present invention, they may possibly be configured such that they do not comprise an internal heat exchanger for energy recovery. Furthermore, the blood treatment/dialysis system comprises at least one drain line through which exhausted cleaning/dialysis fluid can be collected from blood treatment/dialysis machines that are fluidly coupled at the time in question and discharged into a (stationary) drain or a collection tank.

According to the present invention, a (stationary/central) first heat exchanger (WT1) is provided, which is disposed externally to the blood treatment/dialysis machine and which has one side thereof connected to the water supply line or fluid supply line between the water treatment unit and the closest branch connection when seen in the direction of flow or the line section including the branch connections, and which has the other side thereof connected to the drain line and/or the collection tank or the collected exhausted dialysis fluid.

In other words, the present invention is so conceived that, utilizing the thermal energy contained in the exhausted dialysis fluid and making use of a central heating, in particular a heating of the first heat exchanger, the water (permeate/dialysis fluid) in the stationary section/area of the system is heated and provided to the blood treatment/dialysis machines via the water supply line, which is preferably configured as at least one ring line. This entails, in principle, the problem that, when the feed water for the (reverse) osmosis is heated, the risk of microbial contamination in the water treatment unit increases. Since there are normally also maximum temperature limits for osmosis diaphragms, the feed water can only be heated to a limited extent and electric reheating on the part of the blood treatment/dialysis machines would inevitably be necessary. This would restrict the use of energy recovery.

According to the present invention, the water (permeate), which has already been treated, is preheated only downstream of the treatment unit, so that an increase in temperature of the osmosis diaphragm will be avoided.

As has already been outlined hereinbefore, the water supply line defines at least one ring line, which, downstream of the number of branch connections, is returned to the water treatment unit, said ring line being there configured as at least one feedback line. This prevents a loss of non-used, already preheated water (permeate), said water being resupplied to the first heat exchanger for further/renewed preheating via the water treatment unit or immediately downstream thereof.

In addition, a further temperature-transfer/recovery unit may be arranged, which consists of a second heat exchanger disposed externally to the blood treatment/dialysis machines and having one side connected to the water supply line, preferably between the water treatment unit and the first heat exchanger, and the other side connected to the feedback line, preferably between the water treatment unit and the most remote branch connection when seen in the direction of flow or the line section including the branch connections. Alternatively or additionally, a heat pump may be provided, which takes up thermal energy from the drain line and/or the feedback line and transfers useful energy to the water supply line, preferably between the water treatment unit and the closest branch connection when seen in the direction of flow or the line section including the branch connections.

It follows that, with the second heat exchanger, (further) preheating is executed making use of the residual energy in the non-used water (fluid/liquid) conducted through the at least one ring line, whereby the water (fluid) fed back to the treatment unit cools down and heating of the treatment unit (and of the osmosis diaphragm included therein) is avoided. The heat pump has the advantage that also the residual energy in the exhausted dialysis fluid is recycled for transfer to the water (fresh dialysis fluid) of the water supply line. It is in particular such that the heat pump is electronically controllable (with a data management system) so as to increase the temperature of the water (fluid) in the water supply line to a suitable/desired value or so as to lower said temperature (in this case, the heat pump can, vice versa, be operated as a cooling unit).

According to another aspect of the present invention, which may optionally be claimed as an independent aspect, the blood treatment/dialysis system according to the present invention is provided with a central (stationary) electronic control unit (part of the data management system) having connected thereto at least one temperature sensor, which measures the actual temperature in the water supply line at least between the first heat exchanger (WT1) and the line section including the branch connections, the control unit controlling in accordance therewith a heat transfer controller in the area of the first heat exchanger and/or the heat pump so as to accomplish a target temperature, whereby the transferred or transferable amount of heat can be adjusted through the first heat exchanger and/or the heat pump. Excessive heating of the water contained in the ring line can thus be prevented as a matter of principle.

Preferably, the central electronic control unit is, in addition, electrically connected or connectable to the blood treatment/dialysis machines that are fluidly coupled at the time question, so as to obtain information on the prevailing operating phases/operating parameters of these machines and so as to control the heat transfer controller and/or the heat pump in accordance with this information, among other criteria. This feedback allows a (fully automatic) energy management, according to which the temperature of the water contained in the water supply line/ring line is adjusted to a value that reduces to a minimum the individual amount of energy still required for machine-internal heating of the water according to the individual operating phases of the dialysis machines. In this respect, it will be of advantage when the target temperature in the water supply line/ring line is adjusted to the lowest temperature value among the temperature values demanded by the dialysis machines connected at the time question.

Taking all this into account, the effective preparation time of the individual blood treatment/dialysis machines can be reduced by said central heating and control. The temperature of the dialysis fluid (of the fluid) may here be of clinical relevance. For example, hyposentive episodes of hemodialysis patients can be counteracted by cool dialysis fluid.

According to another aspect of the present invention, which may optionally be claimed as an independent aspect, the electronic control unit may intervene directly/indirectly in the operating sequence of the blood treatment/dialysis machines fluidly coupled at the time question, so as to coordinate their prevailing operating phases such that operating phases, in particular those with high electric power consumption, are performed with a time shift in such a way that they temporarily overlap one another as little as possible. Power consumption peaks can thus be avoided/reduced so that the current can, for example, be bought at a less expensive price tariff. In other words, shift working is, for example, common practice in dialysis centers. The temporal sequence is therefore similar. Since a disinfection phase is required for the machines after an extracorporeal blood treatment, the total amount of power required in said centers increases almost cyclically. Since the commonly known energy providers normally charge fees not only for the mere amount of power consumed (in kWh) but also fees depending on temporary peak power consumption, the invention aims at minimizing this peak power consumption. Taking the central electronic control unit according to the present invention so to speak as a data node, it is now possible to communicate the program-controlled heating power in advance.

Disinfection of a blood treatment/dialysis machine comprises e.g. the following phases:
flushing out the dialysis fluid,
preheating,
taking in the disinfectant,
heating the disinfectant solution,
circulating the hot disinfectant solution,
flushing out the disinfectant solution and cooling down the machine.

The heating power required per machine for this process is, at present, between approx. 1,500 to 2,000 W.

By starting the heating phase with a time shift in the range of e.g. 15 minutes, the peak power consumption can be reduced by an average of approx. 20%. The thus generated additional time requirement can normally easily be compensated for through the period of waiting for the next patient (who may also be late) (corresponds to an average idle time). This kind of time shift may also occur when the disinfectant solution is flushed out. Hence, there will also be a reduction of the maximum amount of water consumed per unit time, especially during flushing out.

During the treatment-free period, the dialysis fluid recirculates in said one or said plurality of ring lines. Similar to the refrigerator principle, a reduction of the temperature would result in a decrease in microbial growth (risk of microbial growth). By optionally incorporating the heat pump in combination with the central electronic control unit according to the present invention, this risk can centrally be regulated and controlled on the basis of an adequate cooling operation of the heat pump. In addition, the use of the optional heat pump in the cooling mode allows the temperature of the blood treatment/dialysis machine to be cooled down rapidly and effectively after disinfection/hot cleaning of the blood treatment/dialysis machine.

The provision of the data management system (including the central control) according to the present invention allows also other advantages to be accomplished:

In the case of central disinfection, so-called "inline hot cleaning" is carried out optionally. In so doing, not only the at least one ring line (optionally including the water treatment unit) but also the blood treatment machines are disinfected. Via the data management system according to the present invention, the machines connected at the time in question can be included in the hot cleaning process in the best possible way. This is accomplished by centrally (automatically) controlling the blood treatment machines, in particular after expiration of the heating phase of the water supply. The blood treatment machines then start the intake phase of central hot cleaning with a time shift, so that the temperature in the water supply line is substantially maintained.

Furthermore, the data management system according to the present invention leads to an increase in operational safety and also in the safety of the patient. The data management system (central control) according to the present invention allows, in particular, communication between the treatment unit and the individual blood treatment machines. The treatment unit (reverse osmosis) has additionally supplied thereto data indicating how many blood treatment machines are connected at the time in question and how much water must consequently be provided for these machines. If there should be an abnormal discrepancy between the amount of water supplied to the line system and the amount of water (fluid) returning to the treatment unit, the control unit is adapted to automatically switch off the system and/or generate a warning signal.

Finally, the data management system can be adapted to develop and manage (update) a data collection and to pre-adjust, on the basis of said data collection, the heating unit and/or the heat pump to adequate operating parameters.

DESCRIPTION OF THE DRAWING

The invention is best understood from the following detailed description when read in connection with the accompanying drawing. This FIGURE shows the fluid diagram of a dialysis system as well as the electronic control unit for monitoring and controlling the fluid-mechanical elements of the dialysis system as well as for centrally coordinating the dialysis machines connected at the time in question and the prevailing operating phases thereof.

DETAILED DESCRIPTION OF THE PREFERRED EMBODIMENTS

According to the present invention, the dialysis system as disclosed in the present invention can, in principle, be subdivided into a stationary area and a non-stationary/mobile area. The mobile area essentially concerns dialysis machines which are adapted to be connected to the stationary area separately of one another as well as selectively, or which can be put into operation separately of one another as well as selectively for executing a patient's dialysis treatment. The stationary area comprises, among other components, a pipe system having integrated therein fluidic functional elements (valves, restrictors, filters, etc.) for correctly supplying cleaned/pretreated water to the dialysis machines connected/activated at the time in question as well as for discharging exhausted fluids/liquids, and a central control unit for providing the water in a desired condition (cleaned, tempered, pressurized, etc.) with suitable functional elements (electronic control unit, temperature/pressure sensors, heat exchangers, heat pumps, pressure pumps, etc.).

As regards their respective structural design and their respective function, the dialysis machines essentially correspond to machines known from the prior art, but according to the present invention they may be configured without any heat exchanger or with an internal heat exchanger having only small dimensions. In addition, the dialysis machines each have an electronic I/O interface through which data/information concerning the respective prevailing operating conditions/operating phases can be retrieved from the dialysis machine-internal computer (CPU) and control signals for externally influencing the prevailing operating conditions/operating phases can be input. Insofar, the description following hereinbelow is primarily directed to the stationary area of the dialysis system according to the present invention.

This area first comprises a feed water supply line 1 with an integrated filter, optionally a water softening unit and optionally a restrictor, through which feed water, which is taken from a feed water source (local water supply, water supply well, etc.) and which has been precleaned and reduced to a specific pressure, is supplied to a water treatment unit 2, preferably a reverse osmosis filter unit, at the inlet thereof. In the water treatment unit 2 a water treatment takes place e.g. for converting the feed water into water suitable for use in a dialysis process. Such water treatment units are sufficiently known from the prior art so that it is not necessary to describe them here in more detail.

The outlet of this water treatment unit 2 has connected thereto a supply line 4 for water (fluid/liquid) suitable for use in a dialysis process, said supply line 4 opening into a line section 6 including a number of connection points 10. These connection points (tap connections) 10 have selectively connected thereto blood treatment/dialysis machines 8 having the above-described structural design for fluid communication therewith. When seen in the direction of flow, the line section 6 including the number of connection points 10 merges with a feedback line 12, which leads back into the water treatment unit 2, and in particular to the inlet thereof. A stationary ring line is thus formed, in which water suitable for use in a dialysis process permanently circulates and is subjected again and again to a cleaning process in the water treatment unit 2. Alternatively, it is, however, in principle also possible that the feedback line opens into the supply line for water suitable for use in a dialysis process (which will simply be referred to as water supply line in the following) immediately downstream of the water treatment unit. In this case, the amount of cleaned water supplied from the water treatment unit to the ring line will only suffice to replace the volume tapped off from the connection points. Last but not least, the water supply line and/or the feedback line may have installed therein a pressure pump so as to maintain water circulation at a specific flow rate.

In addition, a collecting line 14 for exhausted dialysis fluid is provided, said collecting line 14 including preferably a number of connection points having the selected dialysis machines 8 connected thereto, so as to discharge exhausted dialysis fluid via the collecting line 14 and get rid of it in a drainage or a tank. This collecting line 14 will therefore also be referred to as sewer line or drain line hereinbelow.

In the water supply line 4 a first stationary heat exchanger WT1 is, on one side WT1/1 thereof, interposed between the water treatment unit 2 and the line section 6 including said number of connection points 10, the other side WT1/2 of said heat exchanger WT1 being interposed in the drain line 14. In this way, heat is extracted from the fluid discharged in the drain line 14, said heat being transferred to the water flowing in the water supply line 4, whereby said water is heated.

Preferably, the first stationary heat exchanger WT1 is adapted to be electronically/electrically controlled with respect to its heat transfer capacity. To this end, the first stationary heat exchanger WT1, or rather its electric closed-loop control device RE, is electrically connected to a central electronic control unit (CPU) CT1. In addition, a number of temperature sensors T1-T4 is connected to the electronic control unit CT1, said temperature sensors being arranged on the water supply line 4 in spaced relationship with one another in the direction of flow, such that at least one respective temperature sensor is positioned upstream and downstream of the first heat exchanger WT1. Preferably, two temperature sensors T1, T4 are arranged downstream of the heat exchanger WT1 and such that they are spaced apart in the direction of flow.

Between the first stationary heat exchanger WT1 and the water treatment unit 2, a second stationary heat exchanger WT2 is, on one side WT2/1 thereof, interposed in the water supply line 4, the other side WT2/2 of said heat exchanger WT2 being interposed in the feedback line 12. One of the temperature sensors T2 is here located on the water supply line 4 between the two heat exchangers WT1, WT2, and another temperature sensor T3 is located on the water supply line 4 between the second stationary heat exchanger WT2 and the water treatment unit 2. In this way, the electronic control unit CT1 is provided with information on the temperature profile along the water supply line 4, from the water treatment unit 2 up to the line section 6 including the branch connection points 10. Furthermore, the central electronic control unit CT1 is electrically connected to the respective I/O interfaces of the dialysis machines 8 that are in fluid communication with the ring line at the time in question, so as to obtain information on the prevailing operating conditions/operating phases of said dialysis machines 8 and so as to controllingly intervene, if necessary, in the prevailing operating conditions/operating phases of said machines according to specific criteria in accordance with the description following hereinbelow.

Last but not least, a stationary heat pump WP is provided, which takes up (residual) thermal energy from the drain line 14 and/or the feedback line 12 and transfers useful energy to the water supply line 4 between the water treatment unit 2 and the line section 6 including the branch connection points 10. More precisely, the heat pump WP takes up residual thermal energy from the fluid flowing in the drain line 14 downstream of the first heat exchanger WT1 and delivers thermal energy to the water flowing in the water supply line 4 downstream of the second heat exchanger WT2, preferably in the area of the first heat exchanger WT1.

The mode of operation of the dialysis system according to the present invention having the above described structural design can be described as follows:

The basic course of action is such that, in the dialysis system according to the present invention, feed water is cleaned in the water treatment unit 2 such that a quality suitable for the subsequent blood cleaning/dialysis treatment is accomplished. Following this, the treated water is conducted into the downstream ring line, in which it flows from the water supply line 4 and the line section 6 including the branch connection points 10 into the feedback line 12 and from said feedback line 12 back into the water treatment unit 2 along a water circulation path.

When flowing through the second heat exchanger WT2 immediately downstream of the water treatment unit 2, the water in the water supply line 4 is first preheated by extracting thermal energy from the feedback line 12 and transferring it to the water supply line 4. The water fed back into the water treatment unit 2 thus arrives there as cold water, so that an increase in temperature of e.g. an osmosis diaphragm in the water treatment unit 2 is avoided.

Subsequently, the water in the water supply line 4 flows through the first heat exchanger WT1, which now transfers, in a controlled manner, thermal energy from the drain line 14, which conveys the exhausted dialysis solution (fluid), to the water supply line 4. In addition, the heat pump WP is optionally operated, said heat pump WP extracting the residual energy, which has not been utilized by the first heat exchanger WT1 and which is still contained in the exhausted dialysis fluid in the drain line 14, and supplies said residual energy to the water supply line section located downstream of the first heat exchanger WT1. Alternatively, the heat pump WP may, however, also be operated vice versa for cooling the water in the ring line, e.g. in the case of a disinfection process in the dialysis machine 8, whereupon the overheated dialysis machine 8 must be cooled down to treatment temperature within the shortest possible time.

Via the temperature sensors T1-T4 upstream of the second heat exchanger WT2 between the first and the second heat exchanger and downstream of the second heat exchanger WT2, the temperature profile along the water supply line 4 can be measured, the measurement results being supplied to the central control unit CT1. The central control unit CT1 also receives information from the dialysis machines 8 connected at the time in question, indicating in particular the operating phase prevailing in the individual dialysis machine 8 and the temperature which the water supplied should therefore have.

Taking this as a basis, the central control unit CT1 determines the respective lowest demanded temperature value as a target value and controls the water temperature via the first heat exchanger WT1 and/or the heat pump WP such that this lowest value demanded by all the dialysis machines 8 connected at the time in question is accomplished. Such central heating and control thus reduces the effective preparation time of the individual dialysis machines 8. In addition, the central control unit CT1 according to the present invention also has more far-reaching possibilities of control.

Shift working is common practice in dialysis centers. The temporal sequence is therefore similar and recurs continuously. Since a disinfection phase is necessary for all dialysis machines 8 whenever a dialysis treatment has taken place, the total amount of power required in said centers cyclically increases disproportionately, especially when a plurality of dialysis machines 8 is in the disinfection phase at the same time. Since energy providers charge fees not only for the mere amount of power consumed but also fees depending on the peak power consumption, it will make sense to avoid or minimize such power peaks.

The energy-intensive disinfection of a dialysis machine normally comprises the following steps:
  flushing out the dialysis fluid,
  preheating,
  taking in the disinfectant,
  heating the disinfectant-water solution (or the disinfectant solution alone),
  circulating the hot solution,
  flushing out the hot solution,
  cooling down the dialysis machine.
The heating power required per machine is between 1,500 to 2,000 W.

As has already been outlined hereinbefore, the central control unit CT1 has supplied thereto information on the operating phases prevailing in the connected dialysis machines 8 and is adapted to intervene in the dialysis machine-internal control such that the peak power consumption can be reduced (by approx. 20% in comparison with synchronized dialysis machines) by starting the above mentioned heating phase with a time shift (e.g. a time shift in the range of approx. 15 minutes). On the basis of the above described communication between the central control unit CT1 and the respective connected dialysis machines 8, the respective time-shifted heating phases also lead to equally time-shifted flushing steps, whereby the maximum amount of water used for the flushing process is reduced as well.

During the dialysis-free period, recirculation of the water in the ring line continues. Similar to the refrigerator principle, a reduction of the temperature can result in a decrease in microbial growth. By incorporating the heat pump WP into the dialysis system according to the present invention in combination with the central control unit CT1, the temperature of the water in the ring line can be reduced to an adequately low value in dialysis machines that are not in operation. As has already been outlined hereinbefore, the heat pump WP can additionally be used for cooling the connected dialysis machines 8 rapidly and effectively after the disinfection phase.

Due to the communication between the stationary water supply (including the water treatment unit) and dialysis technology, an interface is created, which provides, in addition to the above mentioned effects, also other advantages for the user:

In the case of central disinfection, inline hot cleaning can be carried out. In so doing, not only the ring line (optionally including the water treatment unit) but also the dialysis machines are disinfected. The central control unit can be used for adjusting the hot cleaning process such that the dialysis machines will be incorporated in this process in the best possible way. This is accomplished through centrally controlling the respective dialysis machines after expiration of the heating phase of the water supply. The dialysis machines are here caused to start the intake phase of central hot cleaning with a time shift, so that the temperature in the supply line can substantially be maintained. The synchronization of this process is thus effected centrally through the control unit, in contrast to the presently prevailing practice according to which each machine must be programmed individually.

The incorporation of the central control unit in the synchronization/coordination of the operating phase control leads to an increase in safety. In the past, numerous incidents/accidents became known, in the case of which hose connections between the branch connection points and the dialysis machines came off automatically or were damaged, a circumstance that led to serious water damage in the dialysis center. With the aid of the central control unit, however, communication can take place between the individual dialysis machines and the stationary water supply. The water supply or rather its control receives data indicating how many dialysis machines take part in the hot cleaning process and how much water must be provided for this purpose. If the ratio between the water fed into in the ring line and the water returning to the water treatment unit is not correct, the central control unit will be able to conclude that leakage exists and switch off the system e.g. automatically. Cost-intensive damage can be avoided in this way.

Summarizing, it can be stated that a blood treatment/dialysis system is disclosed, which comprises a water treatment unit, preferably of the reverse osmosis type, whose outlet has connected thereto a water supply line provided with a number of branch connections that are fluidly coupled to blood treatment/dialysis machines in a selective manner, and which further comprises a drain line through which exhausted fluid (dialysis fluid) can be discharged from the fluidly coupled blood treatment/dialysis machines. According to the present invention at least one machine-external heat exchanger is provided, which is connected to the water supply line immediately upstream of the branch connections on one side thereof and to the drain line on the other side thereof.

The invention claimed is:

1. An extracorporeal blood treatment system comprising:
 a non-stationary system area including a plurality of blood treatment machines, each of the plurality of blood treatment machines having a respective plurality of operating phases with different operating parameters, wherein the respective plurality of operating phases include at least one of a blood treatment/dialysis phase or a disinfection phase; and
 a stationary system area including:
 a water treatment unit having an outlet connected to at least one water supply line that opens into at least one line section provided with a plurality of connection points and at least one drain line through which exhausted blood treatment/dialysis fluid can be discharged, wherein each of the plurality of blood treatment machines is fluidly coupled to a respective connection point and to the at least one drain line in a selective manner,
 a stationary heating unit disposed externally to the plurality of blood treatment machines and comprising a first heat exchanger (WT1) having a first side (WT1/1) connected to the at least one water supply line between the water treatment unit and the line section including the plurality of connection points, and having a second side (WT1/2) connected to the at least one drain line; and
 a central electronic control unit (CT1) electrically connected to the plurality of blood treatment machines to obtain information on at least the respective plurality of operating phases of each of the plurality of blood treatment machines, and which, in accordance with this obtained information, controls the stationary heating unit connected to the at least one water supply line, such that a target temperature in the at least one water supply line is adjusted to a lowest temperature value of temperature values demanded by the plurality of blood treatment machines, in accordance with the respective plurality of operating phases of each of the plurality of blood treatment machines.

2. The extracorporeal blood treatment system according to claim 1, wherein the central electronic control unit (CT1) has connected thereto at least one temperature sensor, which measures an actual temperature in the water supply line at least between the first heat exchanger (WT1) and the line section including the plurality of connection points and which controls in accordance therewith the stationary heating unit so as to accomplish the target temperature.

3. The extracorporeal blood treatment system according to claim 1, wherein the electronic control unit (CT1) intervenes in an operating sequence of the plurality of blood treatment machines, so as to coordinate the respective operating phases of each of the plurality of blood treatment machines such that operating phases with high electric power consumption are performed with a time shift such that they temporally overlap one another as little as possible, wherein the operating phases with high electric power consumption comprise disinfection phases.

4. The extracorporeal blood treatment system according to claim 1, wherein the water supply line defines at least one ring line, which, downstream of the line section including the plurality of connection points, is returned to the water treatment unit, said ring line being there configured as at least one feedback line.

5. The extracorporeal blood treatment system according to claim 4, wherein the stationary heating unit comprises a further temperature transfer unit including at least one of:
 a second heat exchanger (WT2) disposed externally to at least one of the plurality of blood treatment machines, or
 a heat pump (WP).

6. The extracorporeal blood treatment system according to claim 5, wherein the further temperature transfer unit includes both:
 the heat pump (WP), and
 the second heat exchanger (WT2);
 wherein:
 a first side (WT2/1) of the second heat exchanger (WT2) is connected to the at least one water supply line and a second side (WT2/2) of the second heat exchanger (WT2) is connected to the at least one feedback line, and
 the heat pump (WP) is arranged such that it is adapted to take up thermal energy from at least one of the at least one drain line or the at least one feedback line and transfer the thermal energy to the water supply line.

7. The extracorporeal blood treatment system according to claim 5, wherein the further temperature transfer unit includes the heat pump (WP), and wherein said heat pump (WP) is connected to the at least one drain line downstream of the first heat exchanger (WT1) and transfers thermal energy to the first side (WT1/1) of the first heat exchanger (WT1).

8. The extracorporeal blood treatment system according to claim 5, wherein the further temperature transfer unit includes the heat pump (WP), and wherein said heat pump (WP) is connected to the at least one drain line and the water supply line immediately downstream of the first heat exchanger (WT1).

9. The extracorporeal blood treatment system according to claim 1, wherein the central electronic control unit (CT1) is adapted to receive information with respect to an amount of water taken and to offset the water taken against an amount required by the plurality of connected blood treatment machines so as to determine therefrom an existence of leakage.

10. The extracorporeal blood treatment system according to claim 1, wherein the central electronic control unit (CT1) is adapted to control, in a blood treatment-free operating phase of all connected blood treatment machines, a temperature of a fluid such that the temperature of the fluid lies at a value or in a range of values contributing to a reduction of microbial growth at least in the water supply line.

11. The extracorporeal blood treatment system according claim 1, wherein the central electronic control unit (CT1) collects information, preferably information with respect to a desired temperature, flow and/or quantity of dialysis fluid, a prevailing disinfection phase, and a dialysis-free period and executes on the basis of such information an adequately varying or variable preadjustment for the target temperature.

12. The extracorporeal blood treatment system according to claim 1, wherein the water treatment unit is a reverse osmosis treatment unit.

13. The extracorporeal blood treatment system according to claim 6, wherein:
   the first side (WT2/1) of the second heat exchanger (WT2) is connected between the water treatment unit and the first heat exchanger (WT1),
   the second side (WT2/2) of the second heat exchanger (WT2) is connected between the water treatment unit and the line section including the plurality of connection points, and
   the heat pump (WP) transfers the thermal energy to the water supply line between the water treatment unit and the line section including the plurality of connection points.

14. The extracorporeal blood treatment system according to claim 9, wherein a degree of leakage is further determined.

15. The extracorporeal blood treatment system according to claim 9, wherein the amount required is derived from or calculated on the basis of the respective operating phases.

16. The extracorporeal blood treatment system according to claim 1, wherein the system is a dialysis system, the plurality of extracorporeal blood treatment machines being dialysis machines of mobile construction.

17. The extracorporeal blood treatment system according to claim 9, wherein if the central electronic control unit (CT1) determines the existence of leakage, the central electronic control unit (CT1) is configured to at least one of shut off the extracorporeal blood treatment system or generate a warning signal.

* * * * *